(12) United States Patent
Rebinsky et al.

(10) Patent No.: US 8,653,839 B2
(45) Date of Patent: Feb. 18, 2014

(54) ZINC OXIDE SULFUR SENSORS AND METHOD OF USING SAID SENSORS

(75) Inventors: Douglas Alexander Rebinsky, Peoria, IL (US); Orhan Altin, Dunlap, IL (US); Yong Tian, Peoria, IL (US); Ryan A. Dusheke, Dunlap, IL (US); Luke W. Zinda, Peoria, IL (US); Maggie R. Burrow, Peoria, IL (US); Jedidah Hastings, Peoria, IL (US); Kulasegaram Guga Gugaratshan, legal representative, Dunlap, IL (US)

(73) Assignee: Caterpillar Inc., Peoria, IL (US)

( * ) Notice: Subject to any disclaimer, the term of this patent is extended or adjusted under 35 U.S.C. 154(b) by 0 days.

(21) Appl. No.: 13/354,766

(22) Filed: Jan. 20, 2012

(65) Prior Publication Data

US 2012/0192626 A1    Aug. 2, 2012

Related U.S. Application Data

(63) Continuation-in-part of application No. 12/817,936, filed on Jun. 17, 2010.

(60) Provisional application No. 61/226,401, filed on Jul. 17, 2009.

(51) Int. Cl.
   *G01R 27/08*    (2006.01)

(52) U.S. Cl.
   USPC ........ 324/693; 205/786.5; 73/61.41; 204/422

(58) Field of Classification Search
   USPC ............... 205/781, 786.5; 204/722, 417, 422, 204/426; 73/61.41
   See application file for complete search history.

(56) References Cited

U.S. PATENT DOCUMENTS 4,358,951 A * 11/1982 Chang ................... 73/31.05
4,411,741 A * 10/1983 Janata ................... 257/253

(Continued)

FOREIGN PATENT DOCUMENTS

| JP | 4066857 A | 3/1992 |
| JP | 2004245726 A | 9/2004 |
| JP | 2004294364 A | 10/2004 |
| JP | 2006275950 A | 10/2006 |

OTHER PUBLICATIONS

Preetam Singh, et al., "In Situ high temperature XRD studies of ZnO nanopowder prepared via cost effective ultrasonic mist chemical vopour deposition", Bul. Mater. Sci., vol. 31, No. 3, Jun. 2008, pp. 537-577.

(Continued)

*Primary Examiner* — Richard Isla Rodas
(74) *Attorney, Agent, or Firm* — Miller, Matthias & Hull (57) ABSTRACT

A sensor is disclosed for determining a sulfur concentration in a liquid, such as a liquid fuel. The sensor includes a substrate that is at least partially coated with zinc oxide and, more specifically, zinc oxide microstructures. The zinc oxide microstructures have a crystal lattice structure that is oriented in the (002) plane, are oxygen-deficient and have a rod-like microstructure. If the substrate is conductive, it may be connected directly to a working electrode which is connected to a potentiometer which, in turn, is connected to a reference electrode. If the substrate is non-conductive, the conductive layer can be deposited on the substrate prior to deposition of the zinc oxide to form a working electrode. An application of a constant current (or voltage) to either electrode will result in a voltage across (or current flow between) the working and reference electrodes.

14 Claims, 8 Drawing Sheets

(56) References Cited

U.S. PATENT DOCUMENTS

| | | | |
|---|---|---|---|
| 4,778,769 A * | 10/1988 | Forrest et al. | 436/501 |
| 4,947,104 A * | 8/1990 | Pyke | 324/71.5 |
| 5,111,221 A * | 5/1992 | Fare et al. | 257/414 |
| 5,140,393 A * | 8/1992 | Hijikihigawa et al. | 257/252 |
| 6,716,336 B2 | 4/2004 | Hürland et al. | |
| 6,914,279 B2 * | 7/2005 | Lu et al. | 506/39 |
| 7,079,563 B2 * | 7/2006 | Miyachi et al. | 372/50.12 |
| 7,172,813 B2 | 2/2007 | Burgener, II et al. | |
| 7,261,857 B2 | 8/2007 | Suslick et al. | |
| 7,309,621 B2 * | 12/2007 | Conley et al. | 438/99 |
| 7,498,824 B2 * | 3/2009 | Lane | 324/715 |
| 2003/0217922 A1 * | 11/2003 | Suganuma et al. | 204/426 |
| 2007/0278490 A1 * | 12/2007 | Hirao et al. | 257/64 |
| 2008/0006531 A1 | 1/2008 | Holt | |
| 2009/0286351 A1 | 11/2009 | Hirao et al. | |
| 2011/0012625 A1 | 1/2011 | Hastings et al. | |

OTHER PUBLICATIONS

J.Y. Kim, et al., "Orientations of Polycrystalline ZNO at the Buried Interface of Oxide Thin Film Transistors (TFTs): A Grazing Incidence X-ray Diffraction Study", Bull. Korean Chem. Soc. 2008, vol. 29, No. 4, pp. 727-728.

Yuneng Chang, et al., "Key Factors to Grow (002) Zinc Oxide Films by MOCVD at 320° C and Atmospheric Pressure", Lunghwa University of Science Technology, Dep. of Chemical Engineering, No. 300, Sec. 1, Wanshow Rd., Gueishan, Taoyuan, 333, Taiwan, R.O.C., Apr. 2003.

James R. Connoly, Elementary Crystallography for X-Ray Diffraction, for EPS400-001, Introduction to X-Ray Powder Diffraction, Spring 2007.

Scintag, Inc., "Chapter 7: Basis of X-ray Diffraction", 1999, pp. 7.1-7.25, Cupertino, California USA.

* cited by examiner

500 °C, 2.5 Torr, 50 ml/min O2, 50 ml/min Ar, Precursor T = 145 °C

500 °C, 10 Torr, 50 ml/min O2 and 50 ml/min Ar

500 °C, 2.5 Torr, 50 ml/min O2, 50 ml/min Ar, Precursor T = 30 °C

ZINC OXIDE SULFUR SENSORS AND METHOD OF USING SAID SENSORS

CROSS REFERENCE TO RELATED APPLICATION

This is a continuation-in-part of U.S. application Ser. No. 12/817,936,filed on Jun. 17, 2010, still pending.

TECHNICAL FIELD

This disclosure relates generally to sensors for detecting sulfur concentrations in liquids. More specifically, this disclosure relates to improved zinc oxide sulfur sensors for measuring sulfur concentrations in liquids and methods of manufacturing improved zinc oxide sulfur sensors that may be used by operators in the field.

BACKGROUND

It is important to be able to accurately and reliably measure the concentration of sulfur in liquids, as various chemical reactions may take place that can release harmful sulfur compounds into the atmosphere or onto physical structures around the sulfur-containing liquid. For example, the combustion of diesel fuel typically generates sulfur oxides ($SO_2$, $SO_3$) and sulfuric acid ($H_2SO_4$), which are components of acid rain and subject to environmental regulations. Further, these sulfur compounds have been linked to catalyst poisoning in diesel particulate filters (DPFs) and sulfuric acid may corrode engine components, such as the cooler and piston ring liner components. These phenomena may occur when using both high sulfur (>350 ppm) and low sulfur (15-350 ppm) fuels.

For these reasons, including the sensitivity of after-treatment components to sulfur compounds, many modem diesel engines are now being designed to use ultra low sulfur diesel (ULSD) fuel (<15 ppm S). As a result of these design changes, a low sulfur concentration in diesel fuel is now imperative for optimum performance of many modem diesel engines. While sulfur detection in liquids at levels below 15 ppm is attainable in a laboratory or other test setting, such detection is not currently available in the field with an accurate, portable, reliable, fast and inexpensive sensor. Examples of known means of detecting sulfur at ultra-low levels include flame photometry detection (FPD) and inductively coupled plasma (ICP) devices, but both are more appropriately used in the laboratory setting because of the size of the equipment and the duration of the test cycles.

Accordingly, there is a need for sulfur detection devices that are inexpensive, easy to use and that are capable of fast detection of sulfur concentration in liquids by equipment operators in the field.

SUMMARY OF THE DISCLOSURE

In one example, a sensor is disclosed that determines a sulfur concentration in a liquid. The disclosed sensor may include a substrate that is at least partially coated with zinc oxide. Further, the zinc oxide may have a crystal lattice structure that is oriented in the (002) plane.

In another example, a sulfur concentration detection system is disclosed. The disclosed detection system includes a sensor that may include a working electrode including a substrate coated with zinc oxide. The zinc oxide may include microstructures that have crystal lattice structures oriented in the (002) plane. The sensor may also include a reference electrode. The detection system may also include a current source and a voltage detector, wherein the current source may be connected to the working electrode and the voltage detector may be connected to the reference and working electrodes.

In yet another example, a method for determining a sulfur concentration in a liquid is disclosed. The disclosed method includes exposing the liquid to a sulfur sensor. The sensor may include a working electrode including a substrate, a conductive material and zinc oxide microstructures protruding from the substrate. At least some of the zinc oxide microstructures may have a crystal lattice structure oriented in the (002) plane. The sulfur sensor may also include a reference electrode. The method further includes applying a constant current to the substrate, monitoring a voltage between the working and reference electrodes and correlating the voltage to a sulfur concentration in the liquid.

DETAILED DESCRIPTION

Figure 1:
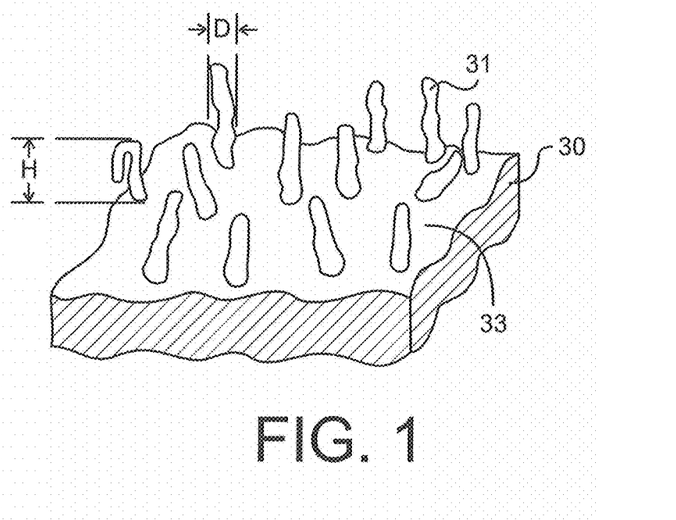
FIG. 1 is a cross-sectional illustration of zinc oxide microstructures on a substrate as disclosed herein.

FIG. 1 shows a cross section of a substrate 30 that is at least partially coated with a plurality of zinc oxide microstructures 31. Under certain conditions and using certain substrates 30 or electrodes, the microstructures 31 may protrude outwardly from the substrate 30. The treatment of the substrate 30 (or electrode) may also impact the morphology of the microstructures 31. While the term "microstructures" is used herein to describe the nature in size of the zinc oxide microstructures, one skilled in the art will understand that the actual scale of the zinc oxide protrusions 31 may approach or enter the nano-scale or alternatively, be larger than the micro-scale.

The substrate 30 may be conductive or non-conductive. Non-conductive substrates 30 may be ceramic or any of a variety of non-conductive substrates that are apparent to those skilled in the art. Conductive substrates may also vary greatly and may eliminate the need for a working electrode 32 (see FIG. 2) or a separate manufacturing step wherein a working electrode 32 is attached or coupled to the substrate 30 and zinc oxide protrusions 31.

Figure 2:
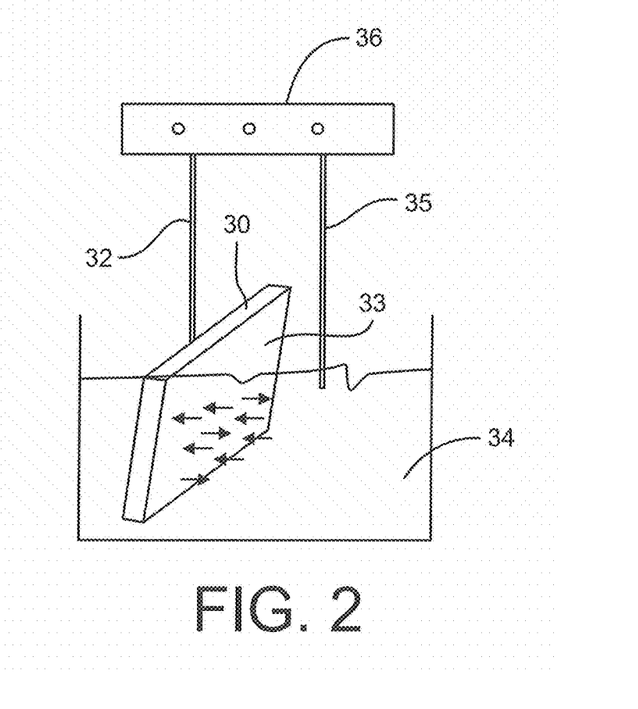
FIG. 2 is a schematic illustration of one method of open circuit potential measurement whereby a disclosed sensor is at least partially submerged in a liquid to be measured and is connected to a working electrode, which is connected to a potentiometer which, in turn, is connected to a reference electrode that is at least partially in the liquid.

The disclosed sulfur sensor is designed based on the physical adsorption of organo-sulfur compounds onto zinc oxide. The inventors have surprisingly found that the rate of physical adsorption of organo-sulfur compounds onto zinc oxide may be a function of the crystallinity of the zinc oxide and, more specifically, the orientation of the crystallinity of the zinc oxide in the (002) plane, or a plane that protrudes vertically upward from the substrate 30 in FIG. 1 or a plane that protrudes horizontally to the right from the surface 33 of the substrate 30 as shown in FIG. 2. As explained below, it has also been surprisingly found that the rate of physical adsorption is also dependent upon the rod-like or ribbon-like morphology of the zinc oxide coating and the oxygen deficiency of the zinc oxide coating.

The physical adsorption of organo-sulfur compounds onto zinc oxide protrusions results in a change in the resistivity of the outer layer of the zinc oxide microstructures. The amount of change of zinc oxide microstructures corresponds directly to the amount of sulfur in the liquid available to react with the zinc in the zinc oxide microstructures 31. This change in resistivity can be measured by measuring a voltage change for a known current applied across the sulfur sensor and the liquid being measured. Of course, the converse is also true; applying a constant voltage across the working and reference electrodes 32, 35 will also result in a constant current flow between the electrodes 32, 35 once the zinc oxide coating becomes saturated with sulfur compounds or in equilibrium with the sulfur concentration in the liquid 34. Further, as shown below, sulfur concentrations can be determined by measuring the amount of time it takes for the voltage to stabilize when a constant current is applied or by measuring the amount of time it takes for the current to stabilize when a constant voltage is applied.

Figure 3:
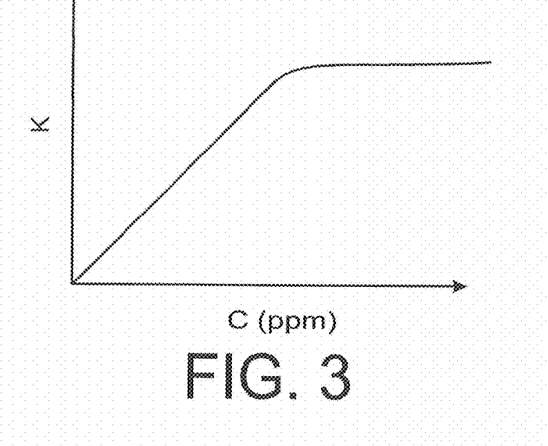
FIG. 3 graphically illustrates the ability of a disclosed zinc oxide sensor to adsorb sulfur until the sulfur concentration reaches a certain value, which is indicative of the concentration of sulfur and the liquid.

Referring to FIG. 2, in one aspect, a substrate 30 with a zinc oxide coating (not shown) on the surface 33 of the substrate 30 is at least partially submerged in a liquid 34. A reference electrode 35 is also at least partially submerged in the liquid 34. The working and reference electrodes 32, 35 are coupled to a potentiometer 36. A known current is applied through the working electrode 32 to the substrate 30 and zinc oxide coating on the surface 33. As the adsorption onto the surface 33 proceeds, an equilibrium will be established based on the concentration of sulfur in the liquid being measured, as illustrated in FIG. 3. Specifically, in FIG. 3, the X axis is the concentration of sulfur in the liquid being measured and the Y axis is the equilibrium constant for the adsorption of the sulfur onto the zinc oxide. As can be seen in FIG. 3, once a certain concentration is reached, the adsorption equilibrium constant remains constant for higher concentrations. Thus, as explained below, depending upon the crystallinity in the (002) plane, the morphology of the zinc oxide microstructures and the oxygen deficiency of the zinc oxide coating, various sensor coatings can be provided that will be effective at various sulfur concentrations.

Figure 4:
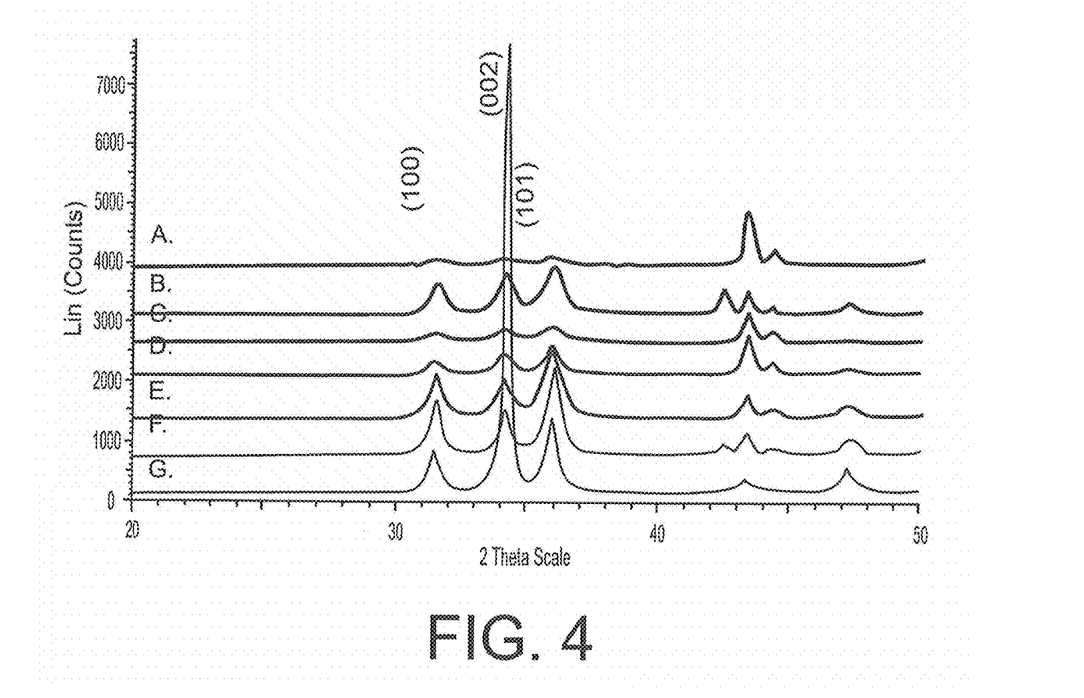
FIG. 4 graphically illustrates x-ray diffraction spectrums for seven different zinc oxide coatings (A-G) that were generated using either different precursors and/or different reaction conditions.

Turning to FIG. 4, x-ray diffraction spectrums are graphically illustrated for seven different samples A-G. Crystallinity in the (002) plane is indicated by a peak at or about 34 along the X axis (2-theta scale). Thus, samples A and C show no or minimal crystallinity along the (002) plane while samples B and D-G show crystallinity along the (002) plane with sample G showing the highest level of crystallinity along the (002) plane.

FIGS. 5-10 compare the abilities of samples A, B and G from FIG. 4 to detect sulfur at concentrations of 15 ppm and 350 ppm. FIGS. 5-10 also illustrate that variations in process parameters can affect the physical characteristics of the zinc oxide coating.

Figure 6:
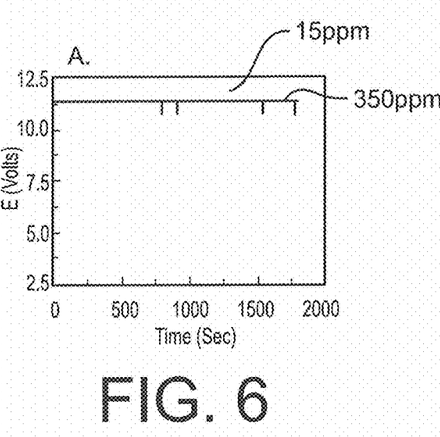
Figure 7:
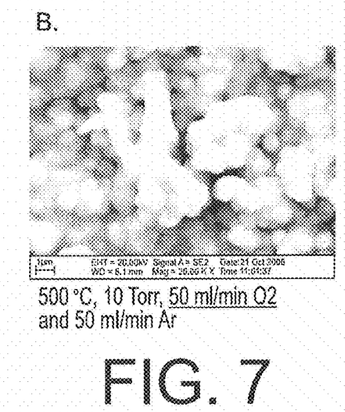
FIG. 7 is a SEM photograph of the microstructures of sample B of FIG. 4 and FIG. 8 graphically illustrates the ability of the microstructures of sample B to adsorb sulfur compounds onto the microstructures of sample B when the sulfur is at a concentration of about 350 ppm.
Figure 8:
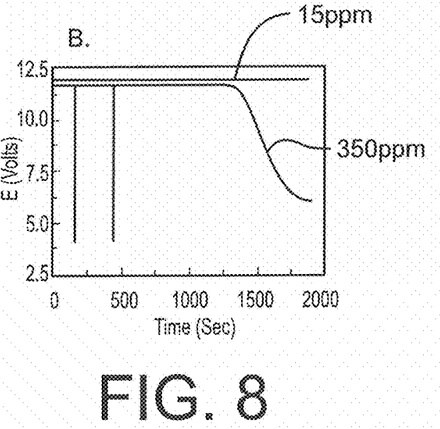

Specifically, the disclosed zinc oxide coatings are prepared using a metal-organic compound vapor deposition (MOCVD) apparatus. Samples A and B were prepared using a zinc acetylacetone precursor, with a chamber temperature of about 500° C, a pressure of about 2.5 ton$^-$, an oxygen flow rate of about 50 ml/min, an argon flow rate of about 50 ml/min and with the zinc acetylacetone precursor temperature of about 145° C. As shown in FIG. 6, the coating of sample A is not effective for measuring sulfur concentrations at either the 15 ppm or 350 ppm concentrations. Turning to FIGS. 7-8, sample B was prepared using a zinc acetylacetone precursor, a chamber temperature of about 550° C, a pressure of about 10 ton and an oxygen and argon flow rates of about 50 ml/min As shown in FIG. 8, sample B is not capable of detecting sulfur levels as low as 15 ppm but is quite capable of detecting sulfur levels at 350 ppm.

Figure 9:
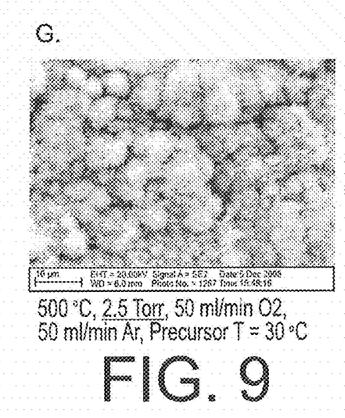
FIG. 9 is a SEM photograph of the microstructures of sample G of FIG. 4 and FIG. 10 graphically illustrates the ability of the microstructures of sample G to adsorb sulfur compounds at least when the sulfur is at a concentration of about 350 ppm.
Figure 10:
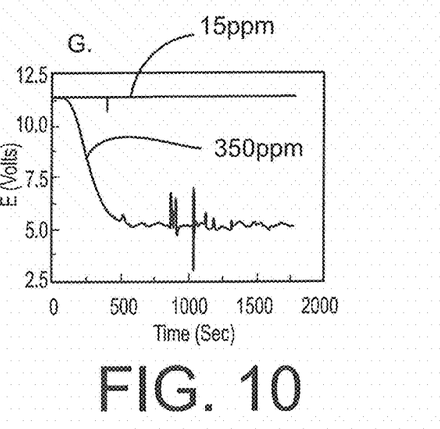

Turning to FIGS. 9-10, a SEM photograph of the coating of sample G is shown in FIG. 9 which was prepared using a diethyl zinc precursor, a chamber temperature of about 500° C, a pressure of about 2.5 torr, oxygen and argon flow rates of about 50 ml/min and a precursor temperature of only about 30° C. As shown in FIG. 10, sample G is capable of quickly detecting a sulfur concentration of 350 ppm, but is not sensitive enough to detect the sulfur concentration of 15 ppm.

Figure 5:
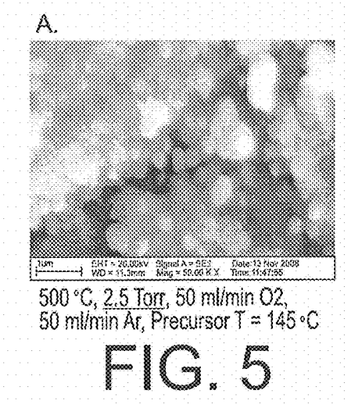
FIG. 5 is a scanning electron microscope (SEM) photograph illustrating microstructures of sample A of FIG. 4 and FIG. 6 graphically illustrates the lack of adsorption of sulfur compounds onto the microstructures shown in the photograph of FIG. 5.

Comparing FIGS. 4-10, it is apparent that zinc oxide coatings with a high crystallinity, such as those exhibited by samples B and D-G, are capable of adsorbing organo-sulfur compounds. Further, it will be noted that the diethyl zinc precursor used for sample G produced a zinc oxide coating that detected sulfur at a concentration of 350 ppm much faster than sample B, which was formed using a zinc acetylacetone precursor. FIGS. 5-6 establish that, without crystallinity along the (002) plane, fast adsorption of organo-sulfur compounds may not be possible, at least at the 15 ppm and 350 ppm concentrations. Thus, FIGS. 4-10 surprisingly illustrate that crystallinity in the (002) plane may be one factor that enhances adsorption of sulfur compounds on zinc oxide coatings.

Figure 11:
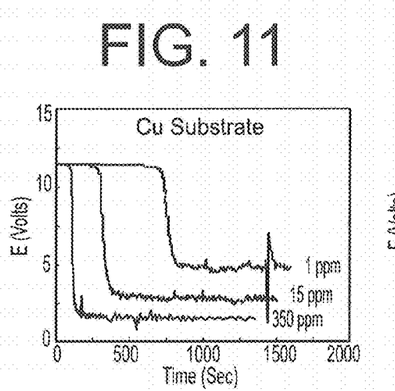
FIG. 11 graphically illustrates the ability of the zinc oxide coating disposed on a copper substrate as shown in the photograph of FIG. 12 to adsorb sulfur compounds in a liquid at concentrations ranging from 1 ppm to 350 ppm.
Figure 12:
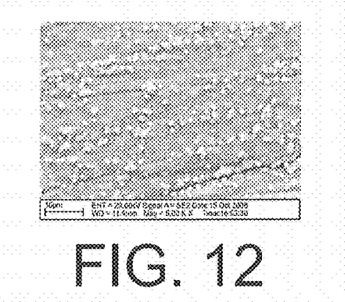
Figure 13:
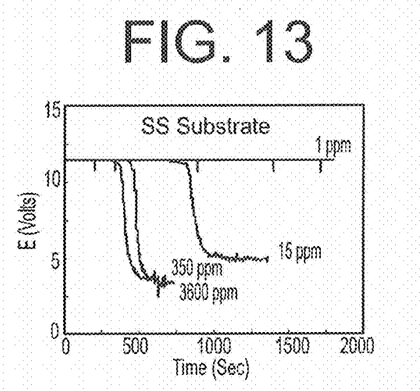
FIG. 13 graphically illustrates the ability of a disclosed zinc oxide coating on a stainless steel substrate as shown in FIG. 14 to adsorb sulfur compounds in a liquid at concentrations ranging from 15 ppm to 3600 ppm.
Figure 14:
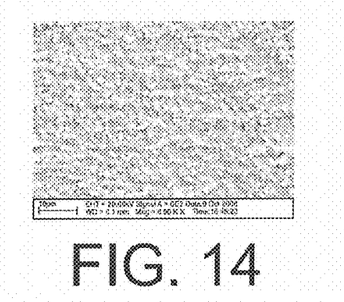

Turning to FIGS. 11-14, comparisons of different substrates and different coating densities are provided. A copper substrate coated with zinc oxide is shown in FIG. 12 and can detect sulfur concentrations of 1, 15 and 350 ppm as shown in FIG. 11. When compared with FIG. 14, the zinc oxide coating of FIG. 12 is less dense than the zinc oxide coating of FIG. 14, which was coated onto a stainless steel substrate and is capable of detecting sulfur concentrations of 15, 350 and 3600 ppm as shown in FIG. 13. The less dense coating of FIG. 12, as shown in FIG. 11, detects sulfur at low concentrations of 1 ppm and 15 ppm as well as at higher concentrations of 350 ppm. The higher concentration of 350 ppm was detected by the coating of FIGS. 11-12 faster than the concentrations at 15 ppm and 1 ppm. In contrast, the dense coating of FIG. 14 cannot detect sulfur at low concentrations of about 1 ppm, but can detect sulfur at higher concentrations of 15 ppm, 350 ppm and 3600 ppm. Thus, from FIGS. 11-14, it can be concluded that denser coatings of zinc oxide are more useful for higher concentrations of sulfur in a liquid and less dense coatings of zinc oxide are more useful for detecting lower concentrations of sulfur in a liquid.

Figure 15:
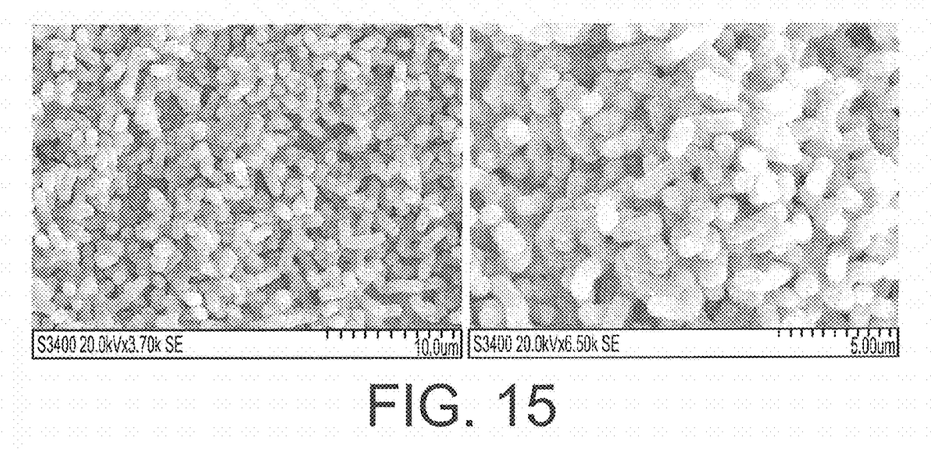
FIG. 15 shows two SEM photographs of different magnifications of a zinc oxide coating that includes rod-like or ribbon-like microstructures that protrude upwardly from the substrate.

Turning to FIG. 15, two SEM photographs, of different magnifications, are shown of the same coating. The sample of FIG. 15 was prepared using a furnace temperature of 500° C. and an increased manifold temperature of 300° C. A zinc acetylacetone precursor was utilized and the coating process was carried out for two hours at a pressure of 10 ton. The argon and oxygen flow rates were 50 ml/min This procedure produced an oxygen deficient zinc oxide coating as shown in FIG. 15, with excellent rod-like structures that protrude upwardly from the substrate (not shown) and therefore have a high crystallinity in the (002) plane. The oxygen deficiency was established by measurement which revealed that the coating of FIG. 15 included 3.31 wt % carbon, 17.9 wt % oxygen, 1.04% chromium, 4.53% iron and 73.22% zinc. The wt % ratio of zinc to oxygen for a fully saturated zinc oxide (ZnO) coating is 3.75, or the molecular weight of zinc (30) divided by the molecular weight of oxygen (8). Hence, the 4.09 ratio (73.22/17.9) of the coating of FIG. 15 is indicative of an oxygen deficient zinc oxide coating.

Figure 16:
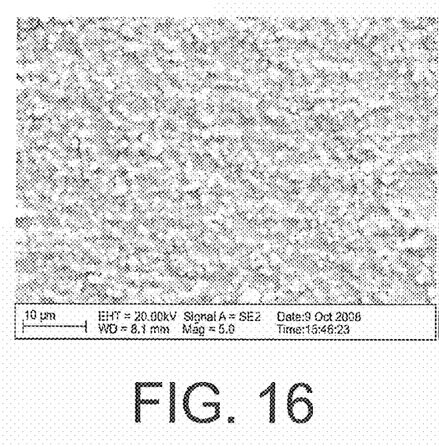
FIGS. 16 and 17 are SEM photographs illustrating the preparation of two zinc oxide coatings at different manifold temperatures, wherein the manifold temperature for the coating of FIG. 16 is 200° C. while the manifold temperature for the coating of FIG. 17 is 300° C, thereby establishing that an increased manifold temperature of FIG. 17 produces rod-like or ribbon-like upwardly protruding microstructures and wherein the lower manifold temperature of FIG. 16 produces shorter and rounder microstructures.
Figure 17:
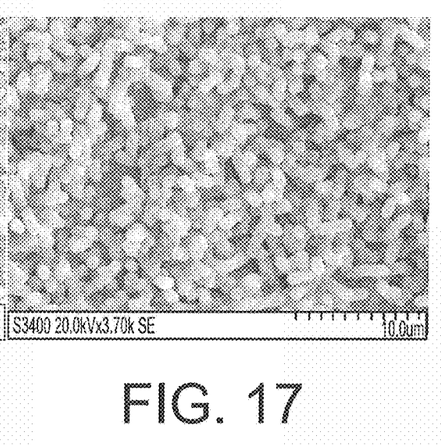
Figure 18:
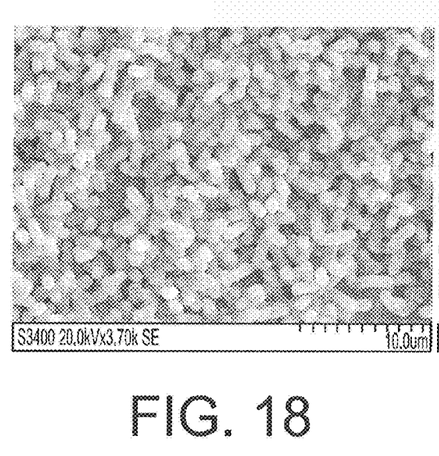
FIGS. 18 and 19 illustrate the effect of reaction time on the microstructures of the zinc oxide coatings wherein the rod-like structures of FIG. 18 have an average thickness of about 0.7 microns and were prepared over a two hour reaction time while the thicker microstructures of FIG. 19 have an average thickness of about 1 micron and were prepared over a 3.5 hour reaction time.
Figure 19:
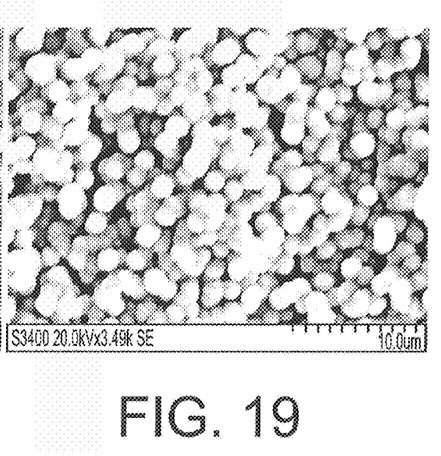

Turning to FIGS. 16-17, the same parameters were used except, in FIG. 16, the manifold temperature was set at 200° C. while the manifold temperature for the coating of FIG. 17 was set at 300° C. Thus, comparing FIGS. 16-17, an increased manifold temperature produces better rod-like microstructures. Turning to FIGS. 18-19, the effects of variations in the reaction time were measured. In FIG. 18, the deposition process was carried out for two hours, which produced the rod-like structures shown in FIG. 18 having an average thickness of about 0.7 microns. However, increasing the reaction time to about 3.5 hours as shown in FIG. 19, produces rod-like structures having an average thickness of about 1 micron. Thus, the less dense coating of FIG. 18 may be preferable for measuring low sulfur concentrations while the more dense coating of FIG. 19 may be more preferable for measuring higher concentrations of sulfur compounds.

Figure 20:
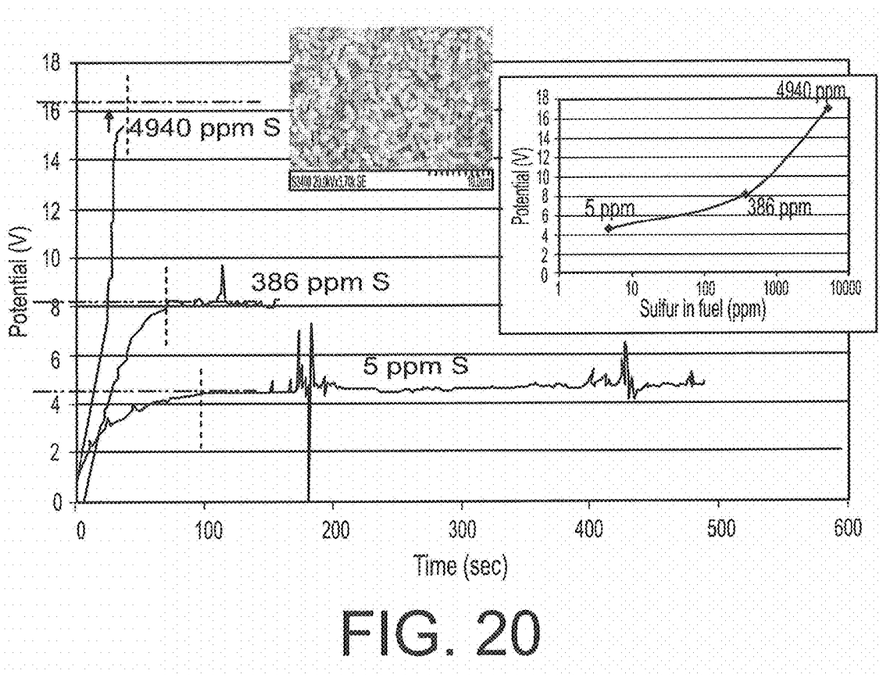
FIG. 20 graphically illustrates the ability of the coating shown in FIG. 18 to adsorb and detect sulfur at a concentration of 5 ppm in about 100 seconds and the ability to adsorb and detect sulfur at a concentration of about 386 ppm in about 80 seconds and FIG. 20 also graphically illustrates the sensitivity of the sensor made from the coating of FIG. 18.

FIG. 20 illustrates, graphically, the response of a sensor coated with the coating of FIG. 18 to liquids having differing amounts of sulfur, specifically 5 ppm and 386 ppm. The voltmeter utilized for the measurements illustrated in FIG. 20 was not capable of detecting more than 15 volts and therefore the combination of the sensor and voltmeter used for FIG. 20 cannot adequately detect a concentration of 4940 ppm as shown in FIG. 20. FIG. 20 also illustrates that the 0.7 micron thick rod-like structures of the coating of FIG. 18 provide a sensor that is suitable for both low sulfur detection (5 ppm) and relatively high sulfur detection (386 ppm). Further, as shown in FIG. 20, the response time for the coating of FIG. 18 is substantially reduced to about 100 seconds for the 5 ppm sulfur concentration liquid and about 80 seconds for the 386 ppm sulfur concentration liquid.

Figure 21:
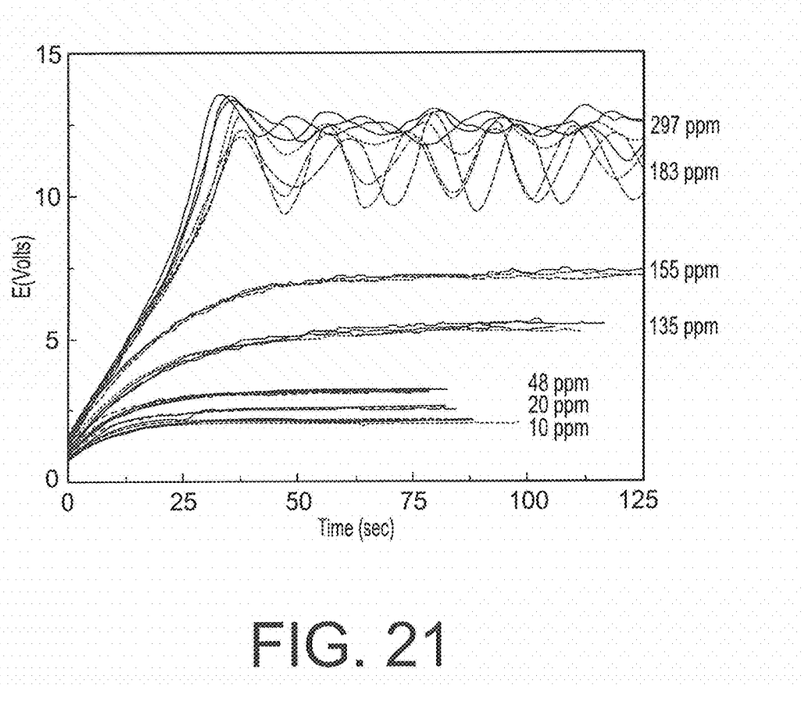
FIG. 21 graphically illustrates the ability of one disclosed zinc oxide sensor to detect sulfur in liquids of concentrations ranging from 10 ppm to 155 ppm and further that such a sensor may have limited effectiveness for sulfur concentrations of 183 ppm or higher.

FIG. 21 illustrates, graphically, the response of the zinc oxide sensor made from sample 106, which is stainless steel, to varying concentrations of sulfur in a liquid, specifically diesel fuels, although this disclosure is directed toward the detection of organic sulfur compounds in any liquid and in any liquid fuel. The sensor illustrated in FIG. 21 provides less sensitivity at the lower concentrations of 10, 20 and 48 ppm but provides substantial sensitivity for the concentrations of 135 and 155 ppm. The sensor illustrated in FIG. 21 is not useful for higher concentrations such as 183 and 297 ppm as the sensor appears to be saturated at those concentrations.

Figure 22:
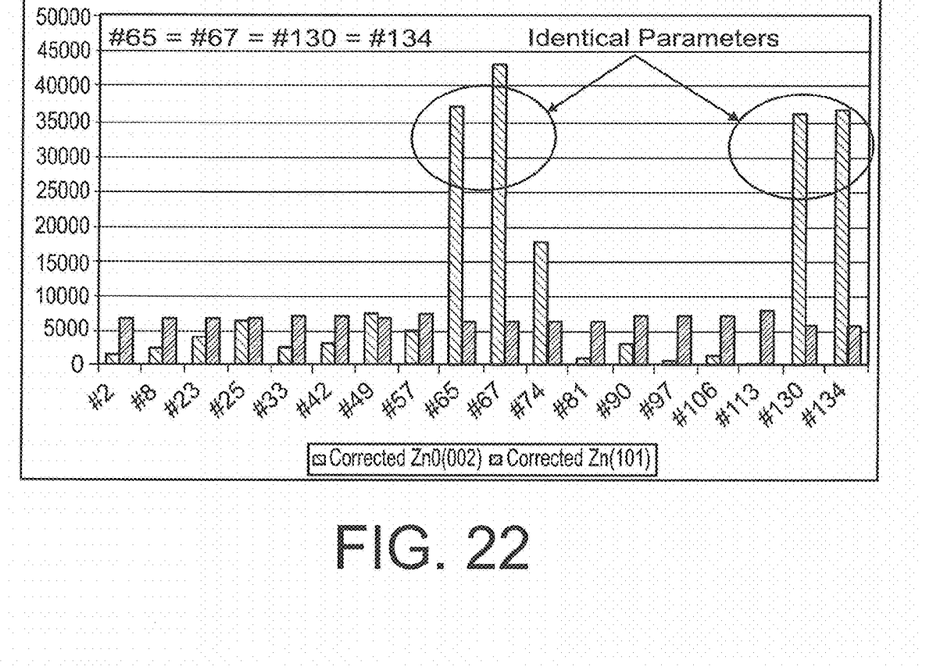
FIG. 22 graphically illustrates the high crystallinity of four zinc oxide coatings in the (002) plane, specifically sample numbers 65, 67, 130 and 134, which were fabricated using identical process parameters.
Figure 23:
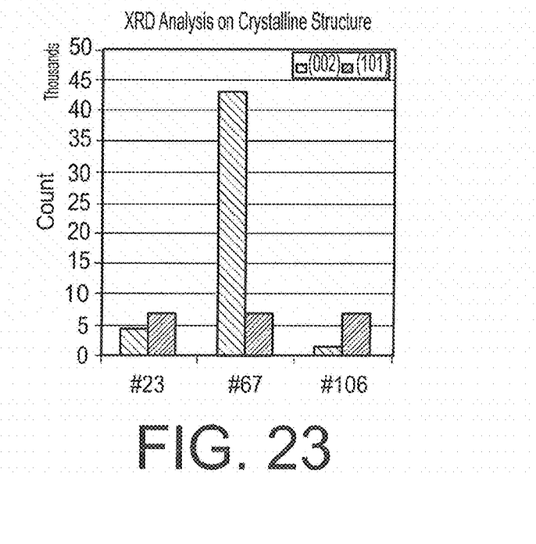
FIG. 23 also graphically illustrates the high crystalline structure in the (002) plane of sample number 67 in comparison to sample numbers 23 and 106.

FIGS. 22-23 are bar graphs of the x-ray diffraction (XRD) analysis of the crystalline structures of zinc oxide coatings made with varying parameters. Specifically, the cycle time, vacuum pressure, bubbler temperature, manifold temperature set point and chamber temperature were all varied. Referring to FIG. 22, identical parameters were used for sample numbers 65, 67, 130 and 134. The parameters used to fabricate the sensor coatings of samples 65, 67, 130 and 134 are presented in the first or left column of Table 1 below. The parameters for the other samples illustrated in FIGS. 22 and 23 are also shown in Table 1.

TABLE 1

| Sample # | 67 | 25 | 49 | 57 | 74 | 90 |
|---|---|---|---|---|---|---|
| Cycle time (hrs) | 7 | 8 | 8 | 5 | 4 | 4 |
| Vacuum pressure (torr) | 15 | 2.5 | 2.5 | 10 | 2.5 | 2.5 |
| Ar flow rate (sccm) | 50 | 50 | 50 | 50 | 50 | 50 |

TABLE 1-continued

| Sample # | 67 | 25 | 49 | 57 | 74 | 90 |
|---|---|---|---|---|---|---|
| $O_2$ flow rate (sccm) | 50 | 50 | 50 | 50 | 50 | 50 |
| Bubbler temp. (° C.) | 125 | 125 | 125 | 125 | 110 | 125 |
| $O_2$ inlet temp. (° C.) | 200 | 250 | 250 | 200 | 200 | 200 |
| Manifold temp. (° C.) | 225 | 265 | 250 | 225 | 225 | 225 |
| Chamber flange temp. (° C.) | 522-527 | 477-487 | 495-499 | 525-532 | 527-529 | 527-529 |
| Corrected (002) | 43119 | 6446 | 7640 | 4777 | 17734 | 3380 |
| Corrected (101) | 6634 | 6939 | 7082 | 7671 | 6536 | 7411 |
| (002)/(001) | 6.5 | 0.93 | 1.08 | 0.62 | 2.71 | 0.46 |

From Table 1, it can be seen that multiple factors have an impact on the (002) crystal lattice orientation. Those factors include cycle time, vacuum pressure, bubbler temperature, manifold temperature and chamber temperature. It appears that the vacuum pressure and cycle time are primary factors and the manifold temperature, bubbler temperature and chamber temperature are secondary factors. With the high ratio of (002) orientation to (101) orientation provided by sample number 67, which was made using the same parameters at samples 65, 130 and 134, it is apparent that maintaining the vacuum pressure somewhat higher, at 15 torr and the cycle time at about 7 hours while maintaining the manifold temperature at about 225° C., the bubbler temperature at about 125° C. and, less importantly, the chamber temperature at about 500° C. will provide zinc oxide microstructures having a strong (002) orientation. Of course, these parameters can be varied greatly and parameters can be chosen for specific applications, such as ultra low sulfur fuels versus high sulfur fuels.

Figure 24:
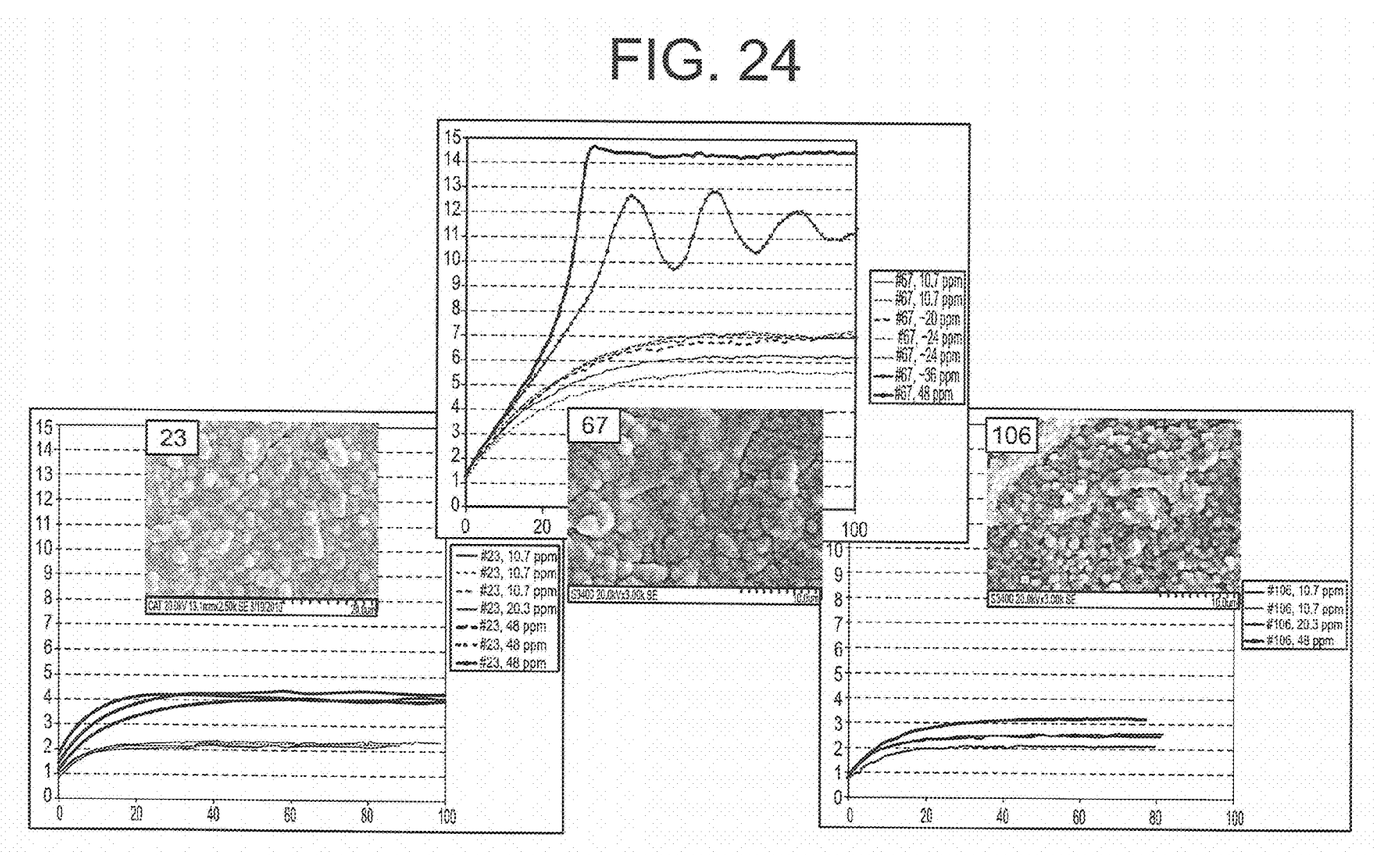
FIG. 24 graphically illustrates the ability of sample 67 to detect sulfur and liquids at low concentrations (10.7 ppm to 48 ppm) and the increased sensitivity of sample 67 with the with the high crystallinity in the (002) plane versus samples 23 and 106, which have low crystallinity in the (002) plane as shown in FIGS. 22-23.

Finally, referring to FIG. 24, it is apparent that sample 67 provides the best sensitivity between the concentrations of 10.7 ppm and 48 ppm. It will also be noted that all samples became saturated or established equilibrium in relatively short time periods. Specifically, while somewhat slower than samples 23 and 106, sample 67 established equilibrium at the higher concentration of 48 ppm in about 30 seconds and established equilibrium at the lower concentrations in about 50 seconds.

Industrial Applicability

The sensors disclosed herein is particularly useful in field applications to allow operators to determine the sulfur content of a fuel before introducing the fuel into a machine that may be designed to run on fuels having specific sulfur concentrations. The sensor disclosed herein may be modified to be disposable, reusable, or as an on-board sensor that determines the sulfur content of the fuel in the fuel tank neck before an appreciable amount of fuel is introduced.

FIG. 21 shows the results of exposing an exemplary ZnO sulfur sensor formed according to this disclosure to a variety of liquids having various sulfur concentrations. Specifically, the ZnO microstructures were formed on a copper substrate using MOCVD. The results in FIG. 21 show how the voltage applied across the sensor and the liquid at a constant current changed over time when the sensor was exposed to liquids having 10, 20, 48, 135, 155, 183 and 297 ppm sulfur. The sensor of FIG. 21 shows good sensitivity for the lower sulfur concentrations (10-155 ppm) while showing poor sensitivity for higher sulfur concentrations (183-297 ppm). As shown in FIG. 20, the sensor illustrated in FIG. 18 shows good sensitivity at both low (5 ppm) and higher (386 ppm) concentrations. The sensor of FIG. 20 reached a saturation point in about 100 seconds for the 5 ppm liquid while the sensor of FIG. 21 reached a saturation point for all concentrations in less than one minute. Thus, the disclosed sensors are fast enough to be used in the field with minimal inconvenience.

As an alternative, an operator may monitor the amount of time necessary for saturation of a ZnO sulfur sensor, as indicated by stabilization of the voltage across the sensor while the current remains constant. The operator could correlate the stabilized voltage to a sulfur content using a lookup table, or the correlation could be automated using known automating techniques, such as a computer accessing a series of lookup tables, and an absolute sulfur reading could be issued to the operator.

To form the ZnO microstructures on a substrate, any suitable deposition and/or growth method known in the art may be used. For example, as noted above, MOCVD may be used to form ZnO deposits on a conductive or ceramic substrate. FIG. 22 and Table 1 show the affect of the vacuum pressure and cycle time or time of the deposition on the (002) crystallinity, while secondary factors are the manifold temperature and bubbler temperature. FIG. 18 shows ZnO microstructures that have been grown over about two hours, whereas FIG. 19 shows ZnO microstructures grown under the same conditions over about 3.5 hours. The thickness of the ZnO micro-structures shown in FIG. 18 is about 0.7 microns and the density is appropriate to allow the ZnO microstructures to grow in highly random directions away from the substrate. By comparison, the thickness of the ZnO microstructures shown in FIG. 19 is about 1.0 microns. While this thickness in itself is acceptable, the density of the ZnO on the surface of the conductive substrate may be too high for low concentrations of sulfur as a high density inhibits interaction between the microstructures and the liquid. Such a high density forces the ZnO microstructures to grow in a highly compact, ordered fashion away from the substrate. Thus, two or more sensors may be employed for fuels of different sulfur concentrations.

While the disclosure has referred to the microstructures as being ZnO microstructures, one skilled in the art should appreciate that the microstructures may have incidental amounts of other elements, likely drawn from the substrate during the deposition and growth process. For example, when the conductive substrate is a stainless steel, the microstructures may have between about 1.0-5.0 wt % C, between about 14.0-24.0 wt % O, between about 0.5-1.5 wt % Cr, and between about 2.5-7.0 wt % Fe, the balance being Zn. In one example, analysis showed that ZnO microstructures grown on a stainless steel substrate had the following composition, by weight percent: C—3.31; O—17.90; Cr—1.04; Fe—4.53; and Zn—73.22.

Regarding the time necessary to accurately detect the sulfur content in the liquid, among other factors, as shown in FIGS. 6, 8, 10, 11, 13, 20-21 and 24, this is highly dependent on the conductivity of the substrate, the total surface area of the ZnO microstructures exposed to the liquid, and the sulfur concentration of the liquid. As can be seen from the data, as sulfur level of the liquid increases, the response time decreases and the stabilized voltage increases when a ZnO sulfur sensor formed per this disclosure is used to test the sulfur level of fuel.

What is claimed is:

1. A sensor for determining a sulfur concentration in a liquid, the sensor comprising:
   a ceramic substrate;
   the ceramic substrate at least partially coated with zinc oxide microstructures; and wherein the zinc oxide microstructures have a crystal lattice structure that is oriented in the (002) plane wherein the zinc oxide microstructures are oxygen deficient and wherein the ceramic substrate and the zinc oxide microstructures are connected to a working electrode.

2. The sensor of claim 1 wherein the zinc oxide microstructures are polycrystalline.

3. The sensor of claim 1 further including a reference electrode.

4. The sensor of claim 1 wherein the zinc oxide microstructures are rod-like or ribbon-like in form.

5. The sensor of claim 4 wherein the zinc oxide microstructures are at least about 0.1 microns wide.

6. The sensor of claim 4 wherein the zinc oxide microstructures are between about 0.1 microns and about 3 microns wide.

7. The sensor of claim 1 wherein the zinc oxide microstructures protrude from the substrate at least about 0.1 micron.

8. The sensor of claim 1 wherein the zinc oxide microstructures protrude from the substrate between about 0.1 micron and about 1.0 mm.

9. The sensor of claim 1 wherein the zinc oxide microstructures cover from about 30% to about 99% of a surface area of the substrate.

10. A sulfur concentration detection system, the detection system comprising:
the sensor of claim 1;
a current source; and
a voltage detector; and
wherein the current source is connected to the working electrode and the voltage detector is connected to a reference electrode and the working electrode.

11. The sulfur concentration detection system of claim 10 wherein the zinc oxide microstructures are rod-like or ribbon-like in form.

12. The sulfur concentration detection system of claim 10 wherein the reference and working electrodes are spaced apart by a gap ranging from about 0.2 to about 0.6 mm.

13. A method for determining a sulfur concentration in a liquid, the method comprising:
exposing the liquid to a sulfur sensor, the sensor including a working electrode including a substrate, a conductive material and zinc oxide microstructures protruding from the substrate, at least some of the zinc oxide microstructures having a crystal lattice structure oriented in the (002) plane, the sulfur sensor also having a reference electrode;
applying a constant current to the substrate;
monitoring a voltage between the working and reference electrodes; and
correlating the voltage to a sulfur concentration in the liquid.

14. The method of claim 13 wherein the liquid is a fuel.

* * * * *